(12) United States Patent
Tansukawat et al.

(10) Patent No.: US 10,723,680 B1
(45) Date of Patent: Jul. 28, 2020

(54) METHOD OF PRODUCING DEUTERATED HALOFORM

(71) Applicant: DeuteroChem Sdn Bhd, Shah Alam, Selangor (MY)

(72) Inventors: Natha Dean Tansukawat, Shah Alam (MY); Alyaa Ezzati Binti Muhammad Hakim See, Shah Alam (MY)

(73) Assignee: DeuteroChem Sdn Bhd, Shah Alam (MY)

( * ) Notice: Subject to any disclaimer, the term of this patent is extended or adjusted under 35 U.S.C. 154(b) by 0 days.

(21) Appl. No.: 16/428,354

(22) Filed: May 31, 2019

(51) Int. Cl.
*C07C 17/361* (2006.01)
*C07C 19/01* (2006.01)
*C07C 19/04* (2006.01)
*B01J 31/02* (2006.01)
*B01J 31/06* (2006.01)

(52) U.S. Cl.
CPC ........... *C07C 19/04* (2013.01); *B01J 31/0244* (2013.01); *B01J 31/06* (2013.01); *C07C 17/361* (2013.01); *C07C 19/01* (2013.01)

(58) Field of Classification Search
None
See application file for complete search history.

(56) References Cited

PUBLICATIONS

Tansukawat, N. D. et al. Method for Small-Scale Production of Deuterochloroform J. Org. Chem. 2018, 83, 8739-8742; Published Jun. 4, 2018 (Year: 2018).*

* cited by examiner

*Primary Examiner* — Medhanit W Bahta
(74) *Attorney, Agent, or Firm* — Bookoff McAndrews, PLLC (57) ABSTRACT

The invention relates to methods of producing deuterated haloform, and apparatus for such methods. In an aspect of the invention, there is provided a method to produce deuterated haloform, the method comprising:

(a) providing a mixture comprising a compound of formula (I)

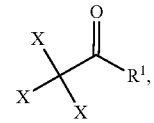

(I)

heavy water, and a catalyst of formula (II),

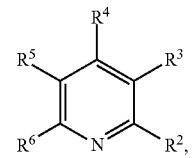

(II)

wherein each X in formula (I) is independently a halogen, and $R^1$ is an aliphatic group, or an aryl group, wherein at least one of $R^2$, $R^3$, $R^4$, $R^5$, and $R^6$ is an anionic functional group, a polymer, or a linker attached to a polymer;
(b) heating the mixture to displace the trihalocarbon anion; and
(c) forming the deuterated haloform.

18 Claims, 7 Drawing Sheets

METHOD OF PRODUCING DEUTERATED HALOFORM

TECHNICAL FIELD

The invention relates to methods of producing deuterated haloform, and apparatus for such methods.

BACKGROUND

Deuterated chloroform ($CDCl_3$) is a common solvent used in nuclear magnetic resonance (NMR) spectroscopy measurements. Industrially, $CDCl_3$ is typically produced through two methods—a reaction of deuterated acetone or ethanol and an alkali metal hypochlorite, or a reaction of chloral hydrate with sodium deuteroxide. Previously reported laboratory scale synthesis of $CDCl_3$ includes reacting chloroform ($CHCl_3$) with deuterium oxide ($D_2O$) and sodium metal or sodium peroxide, or catalytic NaOD. However, the use of sodium metal or sodium peroxide poses a safety hazard on an industrial setting, while the use of catalytic NaOD uses a large excess of deuterium oxide with only a moderate product yield. Another method was to react hexachloro-2-propanone (hexachloroacetone) with pyridine and deuterium oxide, however side products are formed which require distillation to purify the deuterated chloroform. In addition, the side production formation requires the replenishment of pyridine adding to the cost and inefficiency of the process.

SUMMARY OF INVENTION

In an aspect of the invention, there is provided a method to produce deuterated haloform, the method comprises:

(a) providing a mixture comprising a compound of formula (I)

(I)

heavy water, and a catalyst of formula (II), (II)

wherein each X in formula (I) is independently a halogen, and $R^1$ is an aliphatic group, or an aryl group, wherein at least one of $R^2$, $R^3$, $R^4$, $R^5$, and $R^6$ is an anionic functional group, a polymer, or a linker attached to a polymer;

(b) heating the mixture to displace the trihalocarbon anion; and (c) forming the deuterated haloform.

Preferably, each X is chlorine.

Preferably, $R_1$ is $CY_3$, wherein each Y is independently a halogen. More preferably, Y is chlorine. As an example, the compound of formula (I) is hexachloro-2-propanone, and the haloform produced is chloroform.

Preferably, the anionic substituent is selected from a sulfonate, a phosphate, and a carbon/late.

Preferably, the catalyst is a salt of 3-pyridine sulfonate. For example, a Group 1 metal salt like sodium, potassium.

Preferably, the polymer is a vinyl polymer. Vinyl polymers are made from vinyl monomers having a general formula of $CH_2$=CHR, wherein R is the desired or required substituent.

The vinyl polymer may be directly attached to the pyridine group or via the linker. The pyridine moiety is preferably present in each repeating unit of the polymer. More preferably, the $R^4$ substituent is the vinyl polymer. An example of a catalyst is poly(vinylpyridine), specific examples include poly(2-vinylpyridine), poly(3-vinylpyridine), and poly(4-vinylpyridine).

Preferably, the method further comprises purifying the deuterated haloform. More preferably, when at least one of $R_2$, $R_3$, $R_4$, $R_5$, and $R_6$ is the polymer, or the linker attached to the polymer (i.e. the catalyst is a polymer bound pyridine), purifying the deuterated haloform comprises distilling the deuterated haloform and passing the distillate through a sieve with a mesh diameter equal to or less than the particle size of the polymer. This has the advantage of removing any solid particles that may have inadvertently be carried up by the distillate. Further, the mesh may be at a temperature more or less equal to that of the deuterated haloform vapour and condenses compounds with higher boiling points found in the vapour. For example, when the deuterated haloform is chloroform and the compound of formula (I) is hexachloroacetone, the mesh condenses water vapour and hexachloroacetone vapour present in the vapour phase. This along with trapping any catalyst blown over from the reaction vessel are the reasons why the sieve mesh is placed at or near the outlet of the reactor, as will be described in detail below. More preferably, the method further comprises adding a new batch of the compound of formula (I) and heavy water to the mixture. This has the advantage of reusing the catalyst and decreases the overall cost.

Preferably, the method further comprises washing the catalyst with a concentrated chloride solution and drying the catalyst to recycle the catalyst. More preferably, the concentrated chloride solution is a saturated chloride solution, for example saturated sodium chloride (brine) solution, other suitable chlorides may be used. Advantageously, this allows the catalyst to be continuously used for extended periods (for example more than 20 batches) without degradation the catalyst efficiency, turnover rate and require replenishment of the catalyst. The washing of the catalyst possibly removes side product/s formed and restores the catalyst activity. The side product accumulates over multiple batches, slowing down the reaction and wasting the feed chemical, thus it may be sufficient to wash the catalyst after a few batches. For example, the washing may be done when there is a drop in catalytic activity, or at predetermined intervals, for example after five batch runs, after ten batch runs, after twenty batch runs and so forth.

Preferably, the mixture is heated to a temperature of between 70° C. to 105° C., more preferably between 75° C. to 90° C., even more preferably between 80° C. to 90° C. or between 80° C. to 85° C.

Preferably, the catalyst is present in an amount of at least 9 mol % of the compound of formula (I). More preferably, the catalyst is present up to 20 mol % of the compound of formula (I), advantageously avoiding an overly vigorous reaction.

Preferably, the method comprises drying everything in the system from the piping line to the weighing container. More preferably, the method further comprises drying at least one of the following prior to providing the mixture: the compound of formula (I), the catalyst of formula (II) and the reactor or reaction vessel.

Preferably, an amount of compound (I) used is at least 1 mole. More preferably, the amount of compound (I) used is at least 5 moles or at least 10 moles.

More preferably, X is chlorine, and the mixture is heated to a temperature of between 80° C. to 85° C. In an example, $R^1$ is $CCl_3$, in other words the compound of formula (I) is hexachloroacetone, and a reaction temperature of between 80° C. to 85° C. ensures a satisfactory reaction rate, and effectively separates the deuterated chloroform from the reaction mixture and further minimises the heavy water from distilling over.

More preferably, the catalyst is poly(4-vinylpyridine) with a catalyst loading of 0.03 g to 0.08 g of catalyst per gram of the compound of formula (I). In other words, the poly(4-vinylpyridine) has a catalyst loading of 3 to 8 mass % of the compound of formula (I). In another example, the catalyst loading is 0.03 to 0.05 g of catalyst per 1 g of the compound of formula (I).

More preferably, heating the mixture is performed at a pressure of 0.75 psig (1.05 bar or 105 kPa) to 72 psig (6 bar or 600 kPa). Even more preferably, the pressure is from 0.75 psig (1.05 bar or 105 kPa) to 1.75 psig (1.12 bar or 112 kPa). PSIG as used herein is the pressure measured relative to the ambient atmosphere. Advantageously, operating at a slightly higher pressure allows for greater separation of the volatile liquids, in particular between deuterated chloroform and heavy water.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

Ranges expressed herein includes both endpoints unless otherwise stated, and the intervening values between both endpoints. It may be understood that a certain parameter, function, effect, or result can be performed or obtained within a certain tolerance, and the skilled person in the relevant technical field knows how to obtain the tolerance of such term.

DETAILED DESCRIPTION

In the following description, numerous specific details are set forth in order to provide a thorough understanding of various illustrative embodiments of the invention. It will be understood, however, to one skilled in the art, that embodiments of the invention may be practiced without some or all of these specific details. Embodiments described in the context of one of the methods or devices are analogously valid for the other methods or devices. Similarly, embodiments described in the context of a method are analogously valid for a device, and vice versa.

A method to produce deuterated haloform is disclosed. The method comprises providing a mixture comprising a compound of formula (I), heavy water and a catalyst of formula (II); heating the mixture to displace the trihalocarbon anion; and forming the deuterated haloform. The deuterated haloform may be formed by abstracting (or extracting) a deuterium from the heavy water. The deuterated haloform may subsequently be purified by any suitable method. For example, distillation may be used to separate the deuterated haloform and/or reactants from the mixture.

The compound of formula (I) has the following structure:

wherein each X is independently a halogen, and $R^1$ is an alkyl group, a substituted alkyl group, an aromatic group or a substituted aromatic group.

A halogen generally refers to elements in the IUPAC group 17 of the periodic table. The common halogens include fluorine, chlorine, bromine, and iodine. Each X in formula (I) could be the same and/or different. In an example, each X is chlorine.

$R^1$ may be an aliphatic group or an aryl group. In an example, $R^1$ is a $CY_3$ group, where each Y is independently a halogen. This has the advantage of atom efficiency and facile by product removal since the products formed are only the $CX_3D$ and $CY_3D$ (where D is deuterium) and carbon dioxide which escapes from the reaction vessel as a gas. Thus, when X and Y are identical only one product is formed.

The term "aliphatic group" or "aliphatic" refers to a moiety that may be saturated (e.g. single bond) or contain one or more units of unsaturation, e.g., double and/or triple bonds, and in particular refers to the carbon atom forming the bond. An aliphatic group may be straight chained, branched or cyclic, contain carbon, hydrogen or, optionally, one or more heteroatoms and may be substituted or unsubstituted. Non-limiting examples of substituents include a halogen, a hydroxyl, an ether, an amine, a carbamate, a carbonate ester, a urea, an aryl group (e.g. benzyl, phenyl ethyl and the like), a carbonyl, a carboxylic acid, an ester, an amide, a cyano, a nitro, a thiol, a sulfoxide, and a sulfone. It is understood that the substituent may be further substituted.

The term "aryl group" refers to a moiety which includes carbocyclic aromatic rings and heteroaryl rings (nitrogen, oxygen, and sulphur and the like), and in particular refers to the atom forming the bond being part of the ring structure. The term "aromatic group" may be used interchangeably with the terms "aryl", "aryl ring" "aromatic ring", "aryl group" and "aromatic group". The aryl group may be substituted at any one or more substitutable ring atom. Non-limiting examples of substituents include a halogen, a hydroxyl, an ether, an amine, a carbamate, a carbonate ester, a urea, an aliphatic group (e.g. tolyl, mesityl) an aryl group (e.g. biphenyl), a carbonyl, a carboxylic acid, an ester, an amide, a cyano, a nitro, a thiol, a sulfoxide, and a sulfone. Two or more substituents may further form an aliphatic or aryl ring. It is understood that the substituent may be further substituted.

The catalyst of formula (II) has the following structure:

wherein at least one of $R^2$, $R^3$, $R^4$, $R^5$, and $R^6$ is selected from the group: an anionic functional group, a polymer, and a linker attached to a polymer. The $R^2$-$R^6$ substituent makes the catalyst poorly soluble or non-miscible with haloforms in general (and the deuterated version), in particular chloroform, allowing easy separation of the catalyst from the product. Examples of the catalyst include the salt of the sulfonate substituted pyridine and a polymer with a pyridine substituent. The pyridine may be bonded directly to the polymer backbone or via a linker, and each repeating unit of the polymer may contain at least one pyridine moiety. Non-limiting examples of the pyridine bound polymer are the poly(vinylpyridines), with a (—$CH_2CHR$—) repeating unit where R is the pyridine group or a linker with the pyridine group which have a vinyl polymer backbone and the polymer backbone may be referred as the vinyl polymer. Alternatively, the pyridine may be attached to the polymer backbone by a linker, or other polymer backbones may be used, or with cross-linkers in the polymer.

Examples of poly(vinylpyridine) include poly(2-vinylpyridine), poly(3-vinylpyridine) and poly(4-vinylpyridine), with the formulae shown below. Due to possible steric hindrance from the proximity of the pyridine nitrogen to the polymer backbone, poly(4-vinylpyridine) is preferred and may require a lower reaction temperature compared to the other polymer substituted pyridine. The pyridine moiety in the catalyst may be further substituted as well and/or be attached via a linker. In an example, 0.03 g to 0.08 g of one of the 2-,3-,4-substituted polyvinylpyridine (PVP) catalysts may be used per gram of hexachloro-2-propanone (HCP). On a larger scale, 0.03 to 0.05 g of the PVP catalyst may preferably be used per gram of HCP, advantageously this prevents thermal runaway of the reaction on a large scale process which may pose a safety risk and/or lead to lower product yields due to expulsion of the catalyst due to the vigorous reaction. To further lower the risk, 0.03 to 0.04 g of the PVP catalyst may be used.

Formula of poly(2-vinylpyridne)   Formula of poly(3-vinylpyridine)   Formula of poly(4-vinylpyridine):

Heavy water refers to deuterium oxide ($D_2O$), whereby deuterium replaces both hydrogen in a normal water molecule. Tritium is a heavier isotope of hydrogen and may possibly work in the same manner as deuterium.

After the addition of the compound of formula (I), heavy water, and catalyst to a reaction vessel or reactor. The reaction mixture is heated and the catalyst reacts with the compound of formula (I) and displaces the trihalocarbon anion ($CX_3^-$). Alternatively, the reaction mixture may be preheated and the heavy water added upon which the reaction occurs. The trihalocarbon anion extracts a deuterium from the heavy water to form the deuterated haloform. When the $R_1$ group is $CY_3$, it is able to undergo a further reaction with the heavy water (or the deuterated hydroxide anion) to displace a second trihalocarbon anion and carbon dioxide (or carbonic acid). The second trihalocarbon anion further extracts a deuterium to form a second deuterated haloform. Thus, when the compound of formula (I) is symmetrical (both X and Y are chlorine) only one haloform and $CO_2$ is produced in the net equation. Since the catalyst is non-miscible in the haloform, separation of the catalyst from the haloform product is facile. Further, the gaseous carbon dioxide may escape or be vented from the reaction vessel driving the reaction forward.

The deuterated haloform product may be distilled out to purify the product. Alternatively, the heavy water may be distilled out depending on the boiling points of the heavy water and the deuterated haloform, in particular if a substantial amount of the compound of formula (I) has reacted. A pyridine substituted with an anionic functional group or bound to a polymer has significantly higher boiling points than any haloform and provides a substantially simplified method to separate the catalyst from the haloform. Iodoform is the heaviest haloform with a boiling point of 218° C., and deuterated iodoform will have a similar boiling point, thus it is possible for all variants of the haloform to be distilled out. In addition, while iodoform may be distilled out, the low solubility of iodoform in water (and heavy water) may provide an alternative purification method by solid-liquid mixture separation techniques like filtering and decanting.

Figure 1:
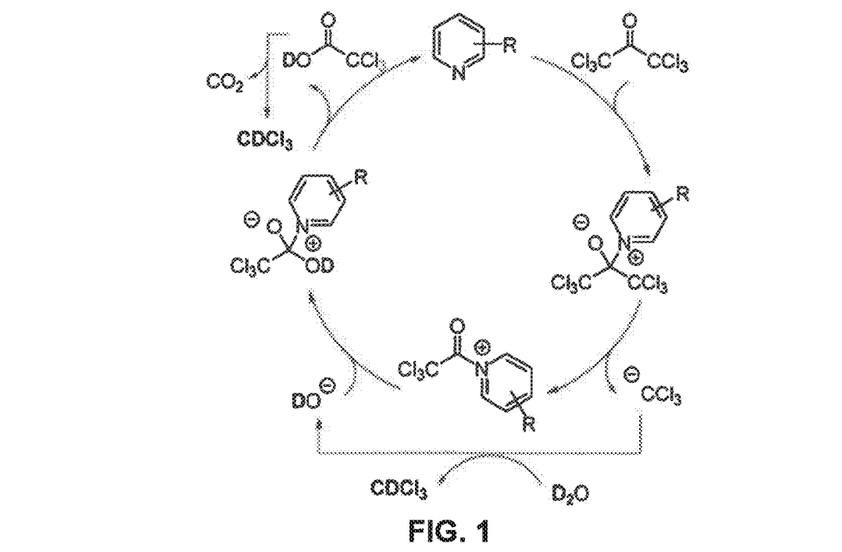
FIG. 1 shows a possible reaction mechanism to produce deuterated chloroform.

FIG. 1 shows a possible reaction mechanism of the reaction between the catalyst and hexachloroacetone as an example. The substituted pyridine catalyst reacts at the carbonyl group of hexachloroacetone to form the tetrahedral intermediate. The trichlorocarbanion is displaced which abstracts a proton from heavy water to form a first molecule of deuterated chloroform. The hydroxide ($DO^-$) displaces the pyridine catalyst, to generate trichloroacetic acid which undergoes decarboxylation to give a second molecule of deuterated chloroform and carbon dioxide. Carbon dioxide escapes from the reaction mixture and drives the reaction equilibrium forwards.

Figure 2:
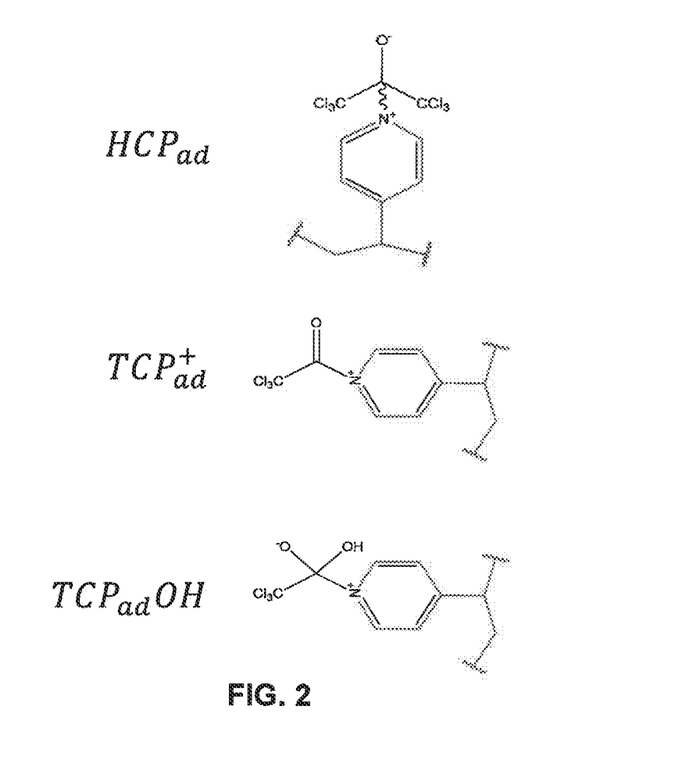
FIG. 2 shows possible intermediates that may be formed in the chloroform production process.

Experiments were conducted to find a potential model to verify the production rate of chloroform and hence deuterated chloroform. FIG. 2 shows three possible intermediates in the reaction mechanism. Based on these possible intermediates, the rate of production of chloroform was determined based on the following rate equations.

$$R_{CHCl_3} = R_3 + R_4 = k_2 C_{H_2O} \hat{C}_{HCP} + k_4 \hat{C}_{TCPOH}$$

$$R_1 = k_1 C_{HCP} C_v - k_{-1} \hat{C}_{HCP} = 0$$

$$\hat{C}_{HCP} = K_1 C_{HCP} C_v; \; K_1 = \frac{k_1}{k_{-1}}$$

$$R_2 = k_2 C_{H_2O} \hat{C}_{HCP}$$

$$R_3 = k_3 C_{OH} \hat{C}_{TCP} - k_{-3} \hat{C}_{TCPOH} = 0$$

$$R_4 = k_4 \hat{C}_{TCPOH}$$

$$\hat{C}_{TCPOH} = \frac{k_2}{k_4} C_{H_2O} K_1 C_{HCP} C_v$$

$$\frac{dC_{CHCl_3}}{dt} = 2k_2 K_1 C_{H_2O} C_{HCP} C_v = K_{overall} C_{H_2O} C_{HCP} C_v$$

Figure 3:
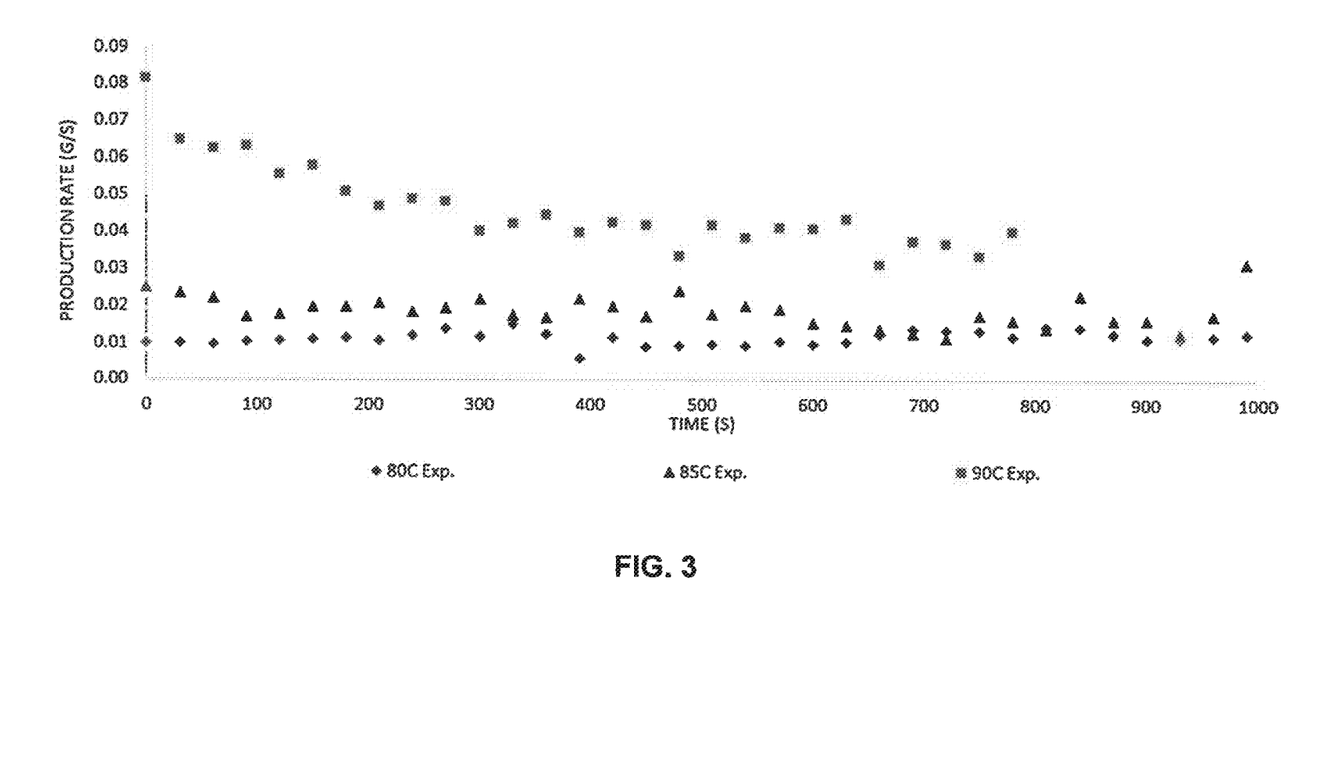
FIG. 3 shows the production rate as a function of time at 80° C., 85° C., and 90° C. with a 5% catalyst loading.
Figure 4:
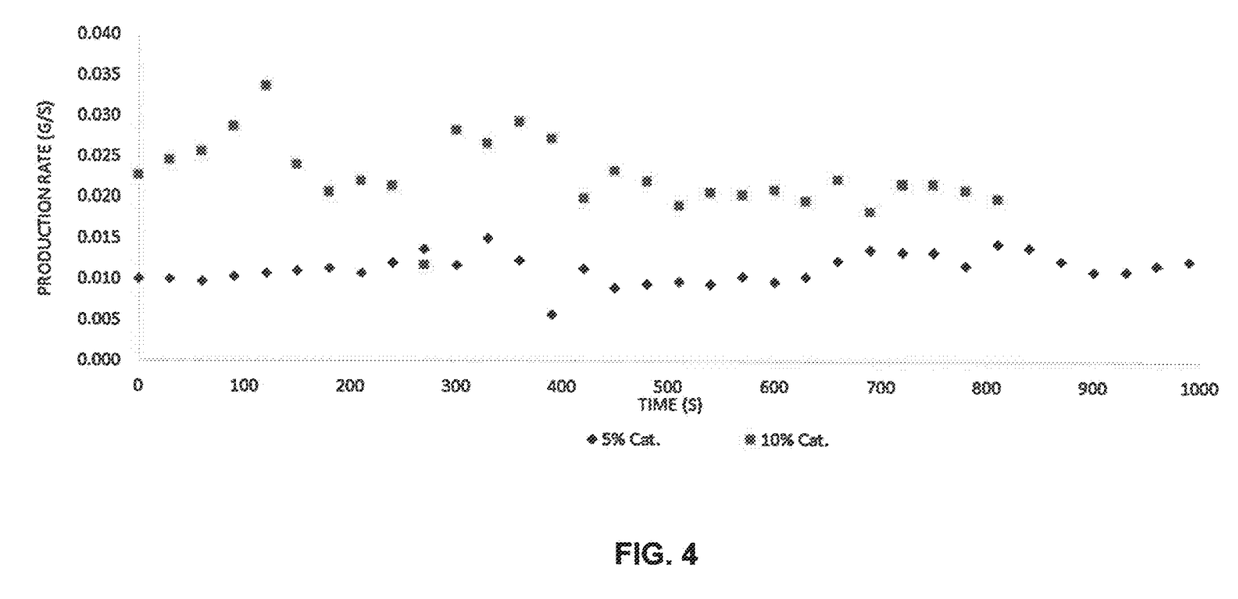
FIG. 4 shows the production rate as a function of time with a 5 mass % and 10 mass % catalyst loading at 80° C.

0.5 mole of HCP and 1 mole of distilled water were reacted with the poly(4-vinylpyridine) catalyst at a loading of 5 mass % and 10 mass % with respect to HCP. The reaction was carried out at different temperatures of 80° C., 85° C. and 90° C. and the results shown in FIGS. 3 and 4. In FIG. 3, it may be seen at a temperature of 90° C., the initial production rate was high and decreased over time, indicating that the temperature may lead to an extremely vigorous reaction initially which may not be desired. On the other hand, the production rates at 80° C. and 85° C. remain fairly constant over time indicating a stable and constant reaction, with the higher temperature providing a slightly higher production rate. In FIG. 4, a comparison between 5% and 10% catalyst loading at 80° C. is shown. It may be observed that the lower catalyst loading provides a generally more constant production rate, while the higher catalyst loading rises and falls in the initial part of the process, thus the higher catalyst loading may not necessarily be the best. These results show that a temperature from 80° C. to 85° C. is preferred, with 85° C. being an optimum temperature with a satisfactory production rate and minimises the water distilling over. If the reaction is overly vigorous the temperature may be slightly lowered. While the production rate increases with catalyst loading, the higher catalyst loading may not necessarily lead to higher yield due to an over vigorous reaction that may lead to runaway of the reaction leading to the mixture contents being expelled from the reaction vessel which leads to an overall decrease in efficiency and yield. As may be seen the results are well modelled by the rate equation (within 7%) and fits the rate equation, thus the model above roughly predicts the experimental results.

The production of deuterated chloroform was subsequently carried out on a small scale initially. The reaction using pyridine (as a control) occurred at 65° C., while SPS required heating to 105° C., it may be that the electron withdrawing nature of the sulfonate group decreased the nucleophilicity of the pyridine catalyst. The heterogeneous PVP catalyst required a temperature of 85° C. due to its lower solubility. The reaction may initiate when the vapour temperature reaches 35° C. and is concluded when the distillate temperature returns to room temperature (25° C.). The potential for catalyst recycling was assessed by adding HCP and more $D_2O$ to the reaction flask (or reaction vessel). Subsequent reactions were deemed complete when the vapour temperature reached back to 25° C. or when the reaction time exceeded twice the initial batch time. The amounts of reagents and catalysts used, and temperature are summarised in Table 1.

TABLE 1

Amounts of Reagents and Catalyst used

| Catalyst | Catalyst amount | HCP | Initial $D_2O$ | $2^{nd}$ aliquot of $D_2O$ | Temperature (° C.) |
|---|---|---|---|---|---|
| Pyridine | 0.491 g (6.20 mmol) | 13.25 g (50.05 mmol) | 2.00 g (100 mmol) | 1.00 g (50.0 mmol) | 65 |
| SPS | 1.124 g (6.20 mmol) | 13.25 g (50.05 mmol) | 3.00 g (150 mmol) | 1.00 g (50.0 mmol) | 105 |
| PVP | 1.0 g (0.017 mmol) | 13.25 g (50.05 mmol) | 2.00 g (100 mmol) | 1.00 g (50.0 mmol) | 85 |

General Experimental Procedure

All glassware used washed with water, acetone, dried in an oven overnight at 130° C., and flame-dried immediately before use and cooled under nitrogen. Chemical reagents were purchased from Sigma-Aldrich. The $D_2O$ used was fresh, poly(4-vinylpyridine) (PVP) was dried overnight in an oven at 80° C., and hexachloropropanone (HCP) (also known as hexachloroacetone) was distilled over $P_2O_5$ into a flash containing 3 Å molecular sieves. Proton NMR spectra were obtained at 25° C. using a Bruker 400 MHz NMR spectrometer, and chemical shifts are reported relative to residual protiated solvent peaks (δ 7.26, 2.49, 7.15 and 4.80 ppm for $CDCl_3$, DMSO-d6, benzene-d6, and MeOD). $^{13}C$ NMR was measured at 100 MHz and chemical shifts are reported relative to residual protiated solvent peaks (δ 77.0, 39.5, 128.0 and 49.0 ppm for $CDCl_3$, DMSO-d6, benzene-d6, and MeOD). Accurate mass measurements were acquired using a Micromass LCT (electrospray ionisation, time-of-flight analyser, or electron impact methods).

Synthesis of $CDCl_3$ Catalysed by Pyridine

Figure 5:
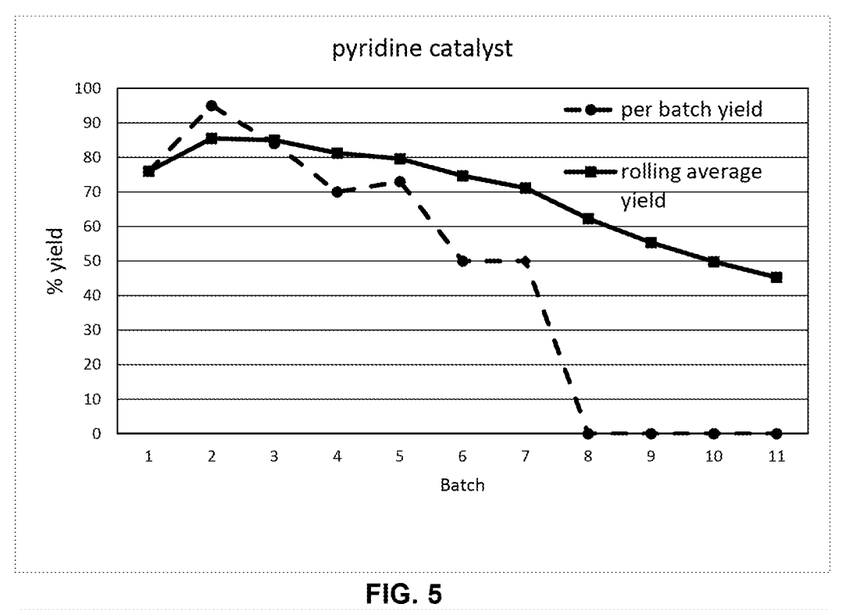
FIG. 5 shows a graph of the percentage yield versus the batch run for pyridine as a catalyst.

A three-neck 50 mL round bottom flask (rbf) was charged with HCP (13.25 g, 50.05 mmol, 1.0 equiv.), and $D_2O$ (2.00 g, 100 mmol, 2.0 equiv., 99.9 atom %). A magnetic stir was added to the rbf and the central ground glass joint was fixed with a distillation head, fractionating column, Liebig condenser, thermometer, and a cooled collection flask. The entire system was flushed with nitrogen gas before the other neck joint were stoppered with rubber septa. The flask was heated to 65° C., during which time, 12 mol % of pyridine (0.49 g, 6.20 mmol, 0.5 mL) was added through the rubber septum using a syringe. Bubbling was observed to occur shortly after the introduction of pyridine and the reaction solution turned a progressively darker brown colour. The temperature was maintained at 65° C. as the distillation progressed, and was continued until the vapour temperature of the distillate dropped back to 25° C. The collected distillate could contain small amounts of pyridine and $D_2O$, depending on the height and type of distillation column. The immiscible $D_2O$ was removed from the $CDCl_3$ using a separatory funnel and returned to the rbf. Trace amounts of pyridine were removed through an additional distillation. The remaining material in the reaction vessel was allowed to cool and subsequent batches were initiated by adding 1 equiv. of $D_2O$ (1.00 g, 50.0 mmol) to the rbf through the septum, followed by a stoichiometric amount of HCP (13.25 g, 50.05 mmol). The order of addition is critical to minimise impurity formation resulting from the reaction of pyridine with HCP. The yields for batches 1-7 were 76% (9.2 g, 76 mmol), 95%, 84%, 70%, 73%, 50% and 50% respectively, after which no further product was obtained presumably due to catalyst decomposition. The results are shown graphically in FIG. 5.

Synthesis of CDCl3 Catalysed by Sodium 3-Pyridine Sulfonate (SPS)

A 50 mL three-neck rbf was charged with HCP (13.25 g, 50.05 mmol, 1.00 equiv.) followed by $D_2O$ (3.00 g, 150 mmol, 3.0 equiv.). A magnetic stir bar was added to the reaction vessel, followed by 12 mol % SPS (1.124 g, 6.20 mmol, 0.12 equiv.) The central ground glass joint was equipped with a 10 mL Dean-Stark apparatus and a Liebig condenser, with rubber septum for the other necks. To the Dean-Stark trap was added $D_2O$ (1.00 g, 50.0 mmol, 1.0 equiv.). The entire system was flushed with nitrogen gas. The rbf was slowly heated to 105° C. and maintained at that temperature for distillation of $CDCl_3$ until no more $CDCl_3$ was being collected in the Dean-Stark trap. The collected $CDCl_3$ distillate was separated from the $D_2O$ with a separatory funnel if necessary, and dried over anhydrous sodium sulfate. The remaining material in the rbf was allowed to cool, and subsequent batches were initiated by adding 1 equiv. of $D_2O$ (1.00 g, 50.0 mmol) followed by a stoichiometric amount of HCP (13.25 g, 50.05 mmol). The yields for batches 1-7 were 67% (8.1 g, 67 mmol), 81%, 85%, 82%, 72%, 69%, and 56% respectively, after which no further product was obtained, presumably due to catalyst decomposition. The results are shown graphically in FIG. 6.

Synthesis of CDCl3 Catalysed by Poly(4-Vinylpyridine) (PVP)

A 50 mL three-neck rbf was charged with HCP (13.25 g, 50.05 mmol, 1.00 equiv.) followed by $D_2O$ (2.00 g, 100 mmol, 2.0 equiv.). A magnetic stir bar was added to the reaction vessel, followed by 1.0 g of PVP with an average molecular weight of 60,000 (19 mol % based on the molecular weight of the repeating unit or 0.075 g of PVP per gram of HCP) The central ground glass joint was equipped with a 10 mL Dean-Stark apparatus and a Liebig condenser, with rubber septum for the other necks. $D_2O$ (1.00 g, 75.0 mmol, 1.0 equiv.) was added to the Dean-Stark trap and the entire system was flushed with nitrogen gas. The rbf was slowly heated to 90° C. and maintained at that temperature for distillation of $CDCl_3$ until no more $CDCl_3$ was being collected in the Dean-Stark trap. The collected $CDCl_3$ distillate was separated from the $D_2O$ with a separatory funnel if necessary, and dried over anhydrous sodium sulfate. The remaining material in the rbf was allowed to cool, and subsequent batches were initiated by adding 1 equiv. of $D_2O$ (1.00 g, 50.0 mmol) followed by a stoichiometric amount of HCP (13.25 g, 50.05 mmol). The yields for batches 1-11 were 62%, 84% (10.1 g, 84 mmol), 80%, 80%, 82%, 82%, 80%, 80%, 84%, 80%, and 82%. The results are shown graphically in FIG. 7.

Determining the Purity of the $CDCl_3$ Product

The purity of the $CDCl_3$ product was determined to be 99.7% D by calculating the ratio of the CHCl3:CDCl3 using a protiated internal standard via quantitative $^1H$ NMR, a deuterated internal standard via quantitative $^2H$ NMR and $^{13}C$ NMR spectroscopy.

The use of pyridine with an anionic functional group substituent or polymer bound simplifies the purification of the haloform, in particular for deuterated chloroform. In the case of pyridine, an initial distillation is required to remove $CDCl_3$ from the vessel. However, if a short-path distillation setup is used, pyridine is found in the distillate and an additional purification step/s is needed. A pyridine substituted with an anionic functional group or bound to a polymer has significantly higher boiling points than any haloform and provides a substantially simplified method to separate the catalyst from the haloform. Iodoform is the heaviest haloform with a boiling point of 218° C., and deuterated iodoform will have a similar boiling point, thus it is possible for all variants of the haloform to be distilled out. In addition, while iodoform may be distilled out, the low solubility of iodoform in water (and heavy water) may provide an alternative purification method by solid-liquid mixture separation techniques like filtering and decanting.

In particular, deuterated chloroform has a boiling point of about 61° C. and may be easily distilled out leaving the catalyst behind. The catalyst remains in the reaction vessel, where it can be charged with additional reagents for continuous use of the catalyst. A Dean-Stark distillation minimises the amount of heavy water required, and the results of the recycling are shown above and in FIGS. 5-7. The potential for recycling the catalysts was assessed by running the reaction ten more times using the original catalyst which remained in the flask, and simply adding a stoichiometric amount of $D_2O$ and a fresh aliquot of HCP to the reaction vessel itself.

Depending on the identity of the pyridine-based catalyst, certain precautions were taken to minimise by-product formation or exothermic reactions. Potential substitution of the haloform and pyridine was minimised by adding the catalyst slowing to the reaction mixture following assembly of the distillation apparatus. To preserve reagent usability, the reaction mixtures using pyridine and SPS as the catalyst were stored in the dark at 10° C. until a fresh charge of HCP and $D_2O$ could be added.

In the case of SPS, additional $D_2O$ was used for the reaction as the catalyst is a salt that does not easily dissolve in HCP. The heterogeneous PVP also presented experimental challenges. In some cases, the temperature of the vapour phase dropped even when the reaction was incomplete. This could be due to PVP catalysing the reaction in "bursts" rather than in a continuous process, perhaps due to the heterogeneous nature of the catalyst. The reaction vessel was not allowed to exceed 90° C. to prevent bumping. After completion of the reaction, the remaining PVP was cooled, removed from the vessel, washed with acetone and stored in an oven at ~100° C.

Pyridine was used as a control to provide a comparison with the other catalysts. With pyridine as the catalyst, the yield per batch was erratic as can be seen in FIG. 1. The results are shown graphically in FIG. 5. Other than the second batch, subsequent batches gave lower yields compared to the first batch, with a significant drop after the 5$^{th}$ batch. For the 8$^{th}$ batch, no product was formed within 3 hours. NMR characterisation of the $CDCl_3$ product showed that some pyridine distilled over along with the desired $CDCl_3$ in the range of 2 mol % to 8 mol %. Thus, the losses in yield as the number of batches increase may possibly be attributed to loss of the catalyst due to co-distillation as well decomposition products resulting from undesired side reactions between pyridine and HCP.

Figure 6:
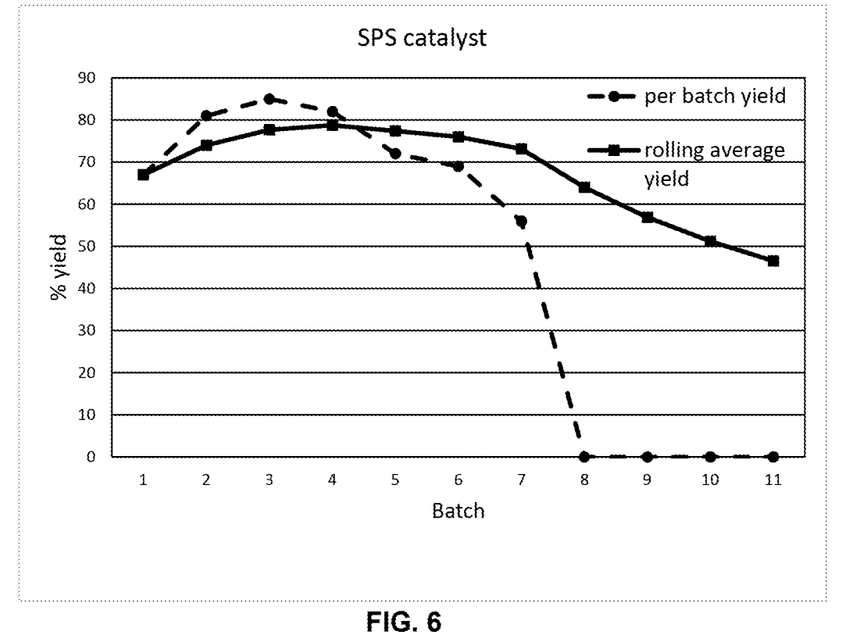
FIG. 6 shows a graph of the percentage yield versus the batch run for sodium 3-pyridine sulfonate (SPS) as a catalyst.

Reactions catalysed by SPS exhibit a similar trend to the pyridine catalysed reactions as shown in FIG. 6. However, SPS delivered a higher yield of $CDCl_3$ over the same number of batches. Further, no impurities were observed by NMR analysis. The reason for the relatively steep drop in yield for the reactions catalysed by pyridine or SPS is believed to be due to the formation of a pyridinium salt by displacement of the chlorine in HCP. This is supported by the formation of an insoluble, dark brown solid, which accumulates as the batch number increases. The solid may entrap the catalyst and block the active site thus leading to decreased reaction rates. Mixing stoichiometric amounts of HCP and pyridine resulted in the formation of a similar solid.

Figure 7:
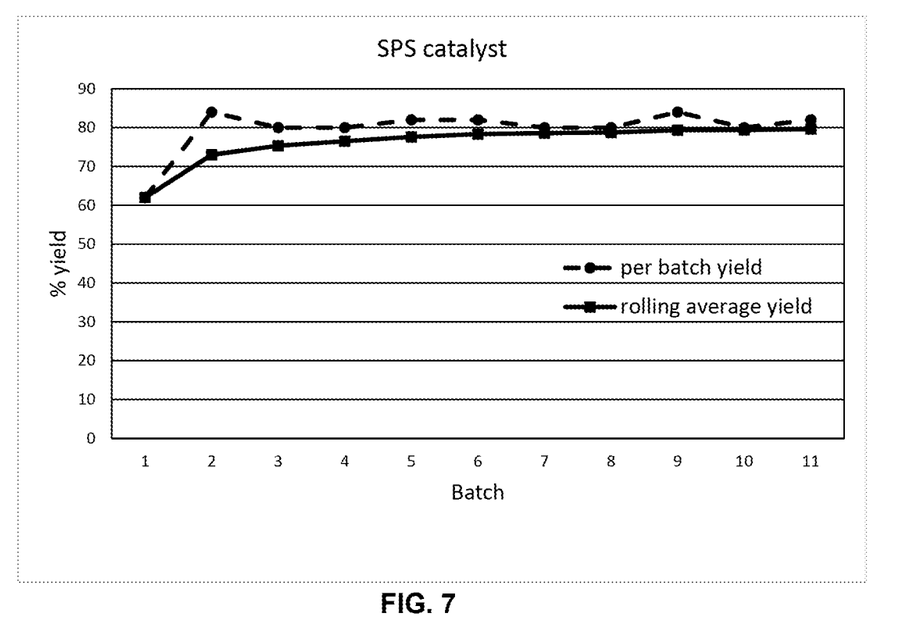
FIG. 7 shows a graph of the percentage yield versus the batch run for poly(4-vinylpyridine) (PVP) as a catalyst.

The reactions catalysed by PVP also produced $CDCl_3$ without any impurities. However as shown in FIG. 7, the PVP catalysed process gave reproducibly high yields through 11 batches, and an overall yield of 79% over 11 batches. In particular, it may be seen that from the $2^{nd}$ to $11^{th}$ batch, the yields were all in a very narrow range of 80 to 84%.

Thus, the results show that although each of the catalysts produces $CDCl_3$ in comparable yield over a single batch, the catalysts differ in terms of their recyclability and ease of purification. The SPS and PVP catalysed reactions afforded a simple and efficient purification method to isolate the deuterated product in high yield. In particular, with deuterated chloroform a single distillation was sufficient to produce the product in high purity. In addition, the PVP catalyst activity remains unchanged even after 11 batches.

Figure 8:
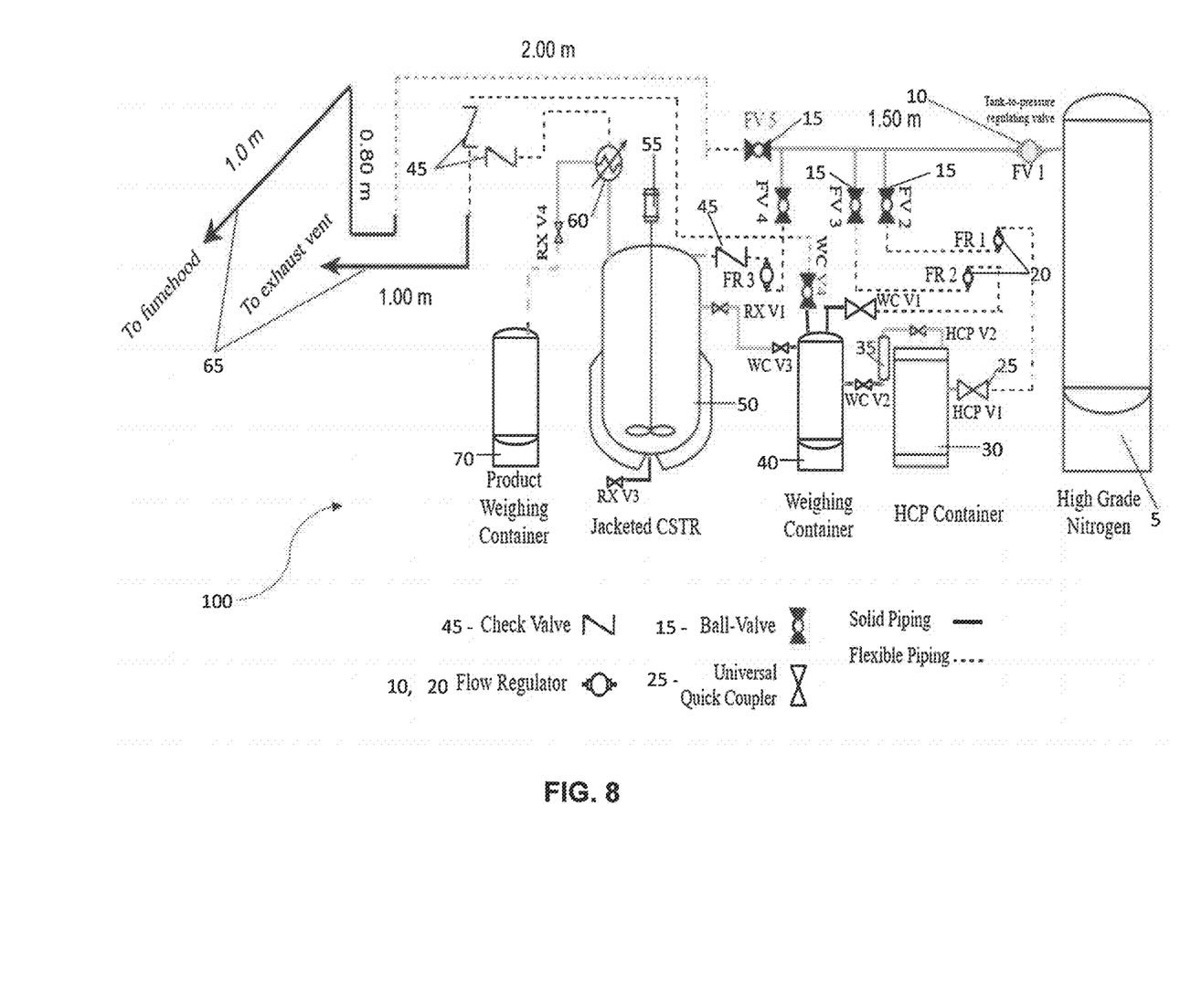
FIG. 8 shows a schematic flow diagram for a system to produce deuterated haloform industrially.

FIG. 8 shows a schematic diagram of a system 100 for a large scale production of the deuterated haloform, in particular deuterated chloroform.

In FIG. 8, it may be seen that the continuous line represents solid piping, while the dashed lines represent flexible piping, and is merely as an example of how the system 100 may be set up. A liquid nitrogen tank 5 (other inert gases may also be used as desired) may be provided with a regulator 10 and ball valve (FV1) which may be opened and close to control flow of nitrogen into the system 100 including the reactor 50 and containers. A pressure relief valve 15 (FV5) may be provided to vent excess pressure in the system out to an exhaust or fumehood 65, for example the pressure relief valve 15 may be configured to relieve the pressure in the feed system at 10 bar.

HCP may be stored in a HCP container 30 and may be flushed with nitrogen via piping, a ball valve 15 (FV2), a flow regulator 20 (FR1) and a universal coupler 25 (HCP V1). In particular, the flow regulator 20 may be used to control the flow of nitrogen into the HCP container 30 to pressurise and dispense the HCP. The HCP container 30 may have a feed outlet connected to a weighing container 40 via piping and quick couplers 25 (HCP V2 and WC V2) to allow the HCP to be dispensed into the weighing container 40. A molecular sieves pipe 35 filled with molecular sieves (for example 3 Å or 4 Å molecular sieves) may be fixed intermediate of the feed outlet such that the HCP is passed through the molecular sieves pipe 35 to dry the HCP before entering the weighing container 40. The weighing container 40 may also be provided with nitrogen via another ball valve 15 (FV3) and a flow regulator 20 (FR2) to flush the weighing container 40. The weighing container may be further provided with a vent outlet with a ball valve 15 (WC V4) and a check valve 45 to allow the HCP container 30 and weighing containers to be pressurised to allow control of the flow of the HCP from the HCP container 30 into the weighing container 40 and subsequently into the reactor 50. The check valve 45 may be used to vent nitrogen out of the system 100 and prevent atmospheric water and/or water vapour from entering via the exhaust 65. The weighing container 40 may be provided with a weighing container outlet connected via quick couplers 25 (WC V3, RX V1) to allow the weighed HCP to be transferred to a reactor 50. A purge outlet with a ball valve may be provided and connected to a heat exchanger 60 (i.e. a condenser) and subsequently vent the system 100 and the individual components via the check valve 45 to the exhaust 65. The heat exchanger 60 condenses the product vapour and allows it to be transferred to a product weighing container 70 for weighing and collecting the distilled haloform in particular chloroform. The check valve allows the excess nitrogen and carbon dioxide (depending on the reactant used) to be vented out.

The reactor 50 may be a jacketed continuous stirred-tank reactor (CSTR), for example a 20 L vacuum adapted reactor, and may have a reactor inlet with a glass plug valve to allow for HCP to be dispensed, an addition port for the other reagents, and a vacuum adaptor port for connection to a vacuum pump. A gas inlet with a glass plug valve, ball valve 15 (FV4), and flow regulator 20 (FR3) may be provided to allow for the reactor to be flushed with nitrogen or other inert gas, and a gas outlet connected to the exhaust 65 may also be provided. Piping may be also be provided to allow for transfer of the deuterated haloform into the product weighing container 70. A drainage outlet with a PTFE needle valve and quick coupler 25 (RX V3) may be provided for the outflow of waste or used catalyst for recycling. The used catalyst may be reactivated to allow the catalyst to maintain its catalytic activity. For example, with the polymer bound pyridine, like poly(4-vinylpyridine), the catalyst may be washed with a saturated sodium chloride solution (or brine solution) to rejuvenate the catalyst. For example, the used catalyst may be transferred from the reactor into a separate vessel, washed with a saturated sodium chloride solution, separate the polymer catalyst and subsequently dried under vacuum before the catalyst is reused again. Advantageously, the catalyst may be used reused for more than 20 batches without replacement under such conditions. Without being limited by theory, it is believed that the chloride ion reacts with the side product/s formed to shift the equilibrium and restore the catalyst, in particular the active site of the catalyst.

Figure 9:
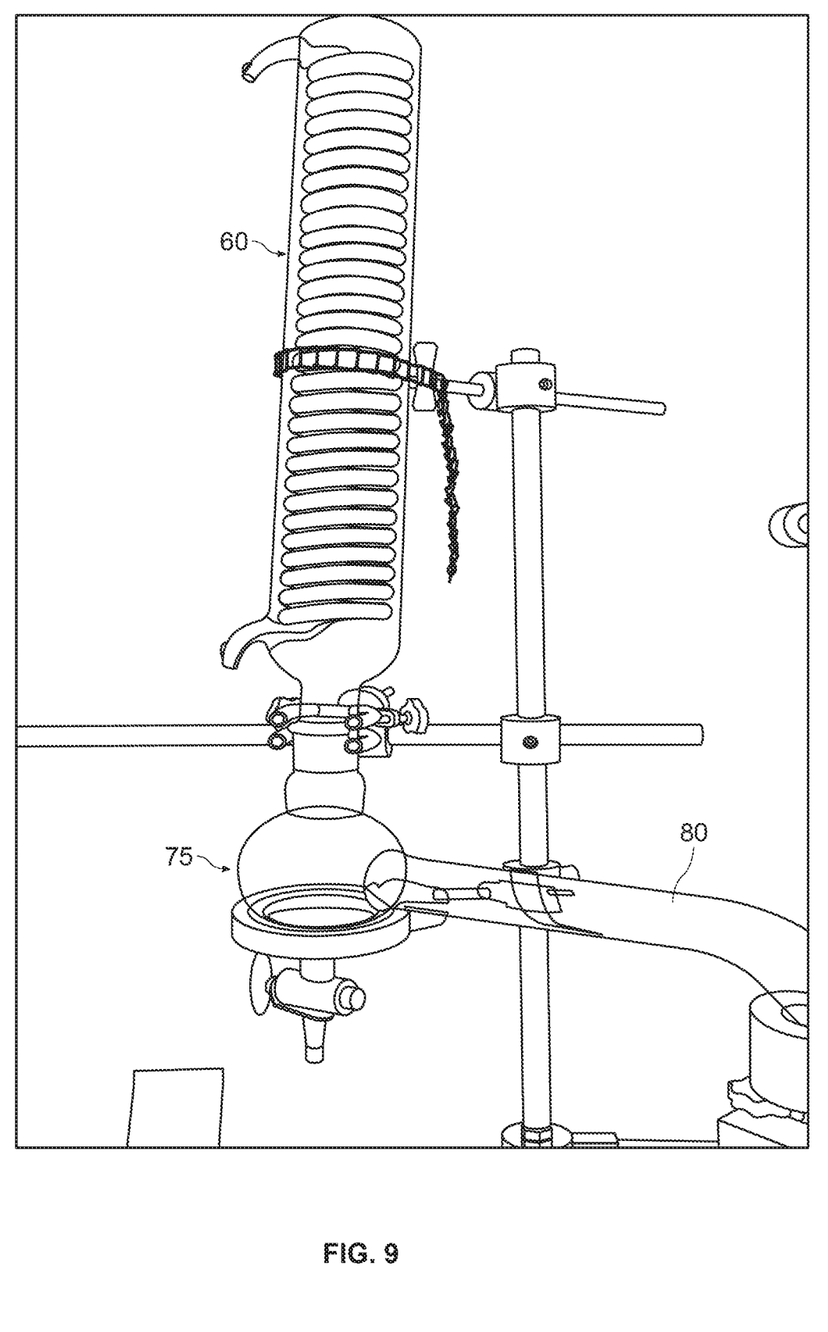
FIG. 9 shows an embodiment of a heat exchanger or condenser for use to produce deuterated haloform.

FIG. 9 shows an example of a heat exchanger or condenser 60 and Dean-Stark trap 75 that may be used in the distillation to collect the product formed. A stainless steel mesh may be provided in the tube portion 80 of the Dean-Stark trap 75 or at the opening in the reactor 50 connected to the tube portion 80. The tube portion 80 connects the reactor 50 and the condenser 60. The bottom of the Dean-Stark trap may be connected via a valve and piping for transfer of the distillate to the product weighing container.

In operation, the regulator 10 is opened and a pressure of about 4 bar may be allowed to flow from the nitrogen tank 5 into the piping. The pressure in the containers 30, 40 and reactor 50 may preferably be regulated to between 0.75 psig to 1.75 psig (105 kPa to 112 kPa). The compressed air may be throttled across the rotameter, dropping its pressure. This will determine the pressure for the entire feed system. The PVP catalyst is dried in an oven at 100° C. 500 g (4.76 mol per repeating unit, 0.13 equiv.) of PVP is scooped into the reactor through the addition port.

To removal excess moisture within the system 100, in particular the weighing container 40 and reactor 50. The reactor 50 may first be heated to 85° C. through the jacketed vessel via the heated water circulator. The heated water circulator may be kept at this temperature throughout the entirety of the operation. Nitrogen may be flushed through the system 100 with the aid of the vacuum and the vacuum adapter port at 3 psig for 10 minutes or until the moisture content in the reactor 50 is below a certain level, for example 0.01%, in particular for the reactor 50 and weighing container 40. A moisture sensor in the gas outlet of the reactor 50 and weighing container 40 may be used to determine moisture content in the reactor 50 and weighing container 40 individually or separately.

Subsequently, the flow regulators 20 and/or ball valves 15 may be closed to prevent any pressurisation of the weighing container 40.

The commercial grade HCP (ChloriTech) used may have a moisture content of 0.04% or less. The purge outlet is first opened followed by the weighing container inlet and then the HCP container feed outlet. Upon allowing the flow of nitrogen into the HCP container 30, the flowing nitrogen causes the HCP to flow from the HCP container 30 through the molecular sieves pipe 35 and into the weighing container 40. The molecular sieves pipe 35 allows for milder operating conditions as the pressure drop across the pipe 35 (or tube) is smaller compared to other drying agents like phosphorus pentoxide which are denser. When about 10 kg (37.8 mol) of HCP is dispensed into the weighing container 40, the nitrogen flow is stopped. Thus, approximately 0.05 g of catalyst is used per gram of HCP. A sample of the HCP is analysed by a Karl-Fischer titration to determine the moisture content meets the requirements, and the mass of the HCP in the weighing container is recorded. If the moisture content is deemed to be acceptable, the HCP is transferred from the weighing container 40 into the reactor 65 similarly by changing the nitrogen pressure.

Based on the amount of HCP added into the reactor, 75.543 g of $D_2O$ per kg of HCP is slowly dripped into the reactor 50 at a temperature of 85° C., with an addition funnel and/or via the addition port. The temperature is preferably kept about between 80° C. to 85° C. to control and prevent an overly vigorous reaction. Deuterochloroform starts to form, vaporise and passes into the Dean-Stark trap 75 and heat exchanger 60, whereby the deuterochloroform condenses back into the Dean-Stark trap and allowed to continue until no more chloroform is produced or collected. The deuterochloroform may be periodically released into the product weighing container 90, or directly collected in a detachable product weighing container 90 connected to the Dean-Stark trap 75. A typical yield will be at least 90%. On a larger production scale, there is sufficient heavy water in the reactor 50 such that heavy water need not be provided in the Dean-Stark trap 75. Further, loss of heavy water stuck in dead spaces in the reactor 50 and associated piping is proportionally much smaller on a large scale.

Subsequently, a second 10 kg batch of HCP may be added via the weighing container 40 into the reactor 50. After each run or multiple runs, or when a drop in catalyst activity is detected, the catalyst may be transferred from the reactor 50 into a separate vessel (for example via the drainage outlet) and washed with a saturated sodium chloride solution. With the polymer bound catalyst, separation from the washing solution is facile, and may be done by filtration or decanting. The washed catalyst is subsequently dried, for example under vacuum before the catalyst is transferred back to the reactor 50. Alternatively, the catalyst may be washed in the reactor 50 and the brine solution drained off via the drainage outlet. The catalyst may then be dried in the reactor and simultaneously remove moisture in the reactor 50. Advantageously, the catalyst may be used reused for extended periods or runs, for example more than 20 batches without replacement under such conditions.

The product may be stored in a brown glass container, and a silver foil may be added to stabilise the product. The container may be filled with nitrogen and sealed. The deuterated chloroform has an isotopic purity of at least 99%, and usually at least 99.5%, and even up to 99.9%. Analysis may be done using mass spectrometry and NMR spectrometry as described above.

Unless defined otherwise or the context clearly dictates otherwise, all technical and Scientific terms used herein have the same meaning as commonly understood by one of ordinary skill in the art to which this invention belongs.

Whilst there has been described in the foregoing description preferred embodiments of the invention, it will be understood by those skilled in the field concerned that many variations or modifications in details of design or construction may be made without departing from the present invention.

The invention claimed is:

1. A method to produce deuterated haloform, the method comprising:
   (a) providing a mixture comprising a compound of formula (I)

heavy water, and a catalyst of formula (II), wherein each X in formula (I) is independently a halogen, and $R^1$ is an aliphatic group or an aryl group,
wherein at least one of $R^2$, $R^3$, $R^4$, $R^5$, and $R^6$ is a polymer, or a linker attached to the polymer;
   (b) heating the mixture to displace the trihalocarbon anion;
   (c) forming the deuterated haloform; and
   (d) purifying the deuterated haloform, wherein purifying the deuterated haloform comprises distilling the deuterated haloform to form a distillate, and passing the distillate through a sieve with a mesh diameter equal to or less than a particle size of the polymer.

2. The method of claim 1, wherein X is chlorine.

3. The method of claim 1, wherein $R^1$ is $CY_3$, wherein each Y is independently a halogen.

4. The method of claim 1, wherein the anionic substituent is selected from the group consisting of a sulfonate, a phosphate, and a carboxylate.

5. The method of claim 1, wherein the catalyst is a salt of 3-pyridine sulfonate.

6. The method of claim 1, wherein the polymer is a vinyl polymer.

7. The method of claim 6, wherein the $R^4$ substituent is the vinyl polymer.

8. The method of claim 6, wherein the catalyst is poly(4-vinylpyridine).

9. The method of claim 1, further comprising adding a new batch of the compound of formula (I) and heavy water to the mixture.

10. The method of claim 9, further comprising washing the catalyst with a concentrated chloride solution and drying the catalyst to recycle the catalyst.

11. The method of claim 1, wherein the mixture is heated to a temperature of between 70° C. to 105° C.

12. The method of claim 1, wherein the mixture is heated to a temperature of between 80° C. to 90° C.

13. The method of claim 1, wherein the catalyst is present in an amount of at least 9 mol % of the compound of formula (I).

14. The method of claim 1, further comprising drying at least one of the following prior to providing the mixture: the compound of formula (I), the catalyst of formula (II) and the reactor or reactive vessel.

15. The method of claim 1, wherein an amount of compound (I) used is at least 1 mole.

16. The method of claim 14, wherein X is chlorine, and the mixture is heated to a temperature of between 80° C. to 85° C.

17. The method of claim 15, wherein the catalyst is poly(vinylpyridine) with a catalyst loading of 0.03 g to 0.08 g of catalyst per 1 g of the compound of formula (I).

18. The method of claim 15, wherein heating the mixture is performed at a pressure of 105 kPa to 500 kPa.

* * * * *